(12) United States Patent
Wahlstrom et al.

(10) Patent No.: US 11,976,420 B2
(45) Date of Patent: May 7, 2024

(54) REINFORCED PAPER FOR PACKAGING OF MEDICAL DEVICES

(71) Applicant: BILLERUD AKTIEBOLAG (PUBL), Solna (SE)

(72) Inventors: Lars Wahlstrom, Norrkoping (SE); Paul Turner, Lancashire (GB)

(73) Assignee: PELTA MEDICAL PAPERS LTD, Milnthorpe (GB)

( * ) Notice: Subject to any disclaimer, the term of this patent is extended or adjusted under 35 U.S.C. 154(b) by 87 days.

(21) Appl. No.: 17/417,093

(22) PCT Filed: Dec. 18, 2019

(86) PCT No.: PCT/EP2019/086134
§ 371 (c)(1),
(2) Date: Jun. 21, 2021

(87) PCT Pub. No.: WO2020/136064
PCT Pub. Date: Jul. 2, 2020

(65) Prior Publication Data
US 2022/0049427 A1 Feb. 17, 2022

(30) Foreign Application Priority Data
Dec. 27, 2018 (EP) .................... 18248106

(51) Int. Cl.
| | | |
|---|---|---|
| *D21H 13/24* | (2006.01) |
| *D21H 11/04* | (2006.01) |
| *D21H 17/28* | (2006.01) |
| *D21H 17/33* | (2006.01) |
| *D21H 19/22* | (2006.01) |
| *D21H 21/18* | (2006.01) |
| *D21H 27/10* | (2006.01) |

(52) U.S. Cl.
CPC .............. *D21H 13/24* (2013.01); *D21H 11/04* (2013.01); *D21H 17/28* (2013.01); *D21H 17/33* (2013.01); *D21H 19/22* (2013.01); *D21H 21/18* (2013.01); *D21H 27/10* (2013.01)

(58) Field of Classification Search
CPC ........ D21H 27/10; D21H 11/04; D21H 13/34; D21H 17/28; D21H 19/54; D21H 19/22; D21H 21/18
USPC ...................................... 162/157.3
See application file for complete search history.

(56) References Cited

U.S. PATENT DOCUMENTS

| | | |
|---|---|---|
| 5,223,095 A | 6/1993 | Kinsley |
| 6,808,691 B1 | 10/2004 | Herve et al. |
| 2002/0090474 A1 | 7/2002 | Bean et al. |
| 2010/0173138 A1 | 7/2010 | Williams et al. |

FOREIGN PATENT DOCUMENTS

| | | | |
|---|---|---|---|
| EP | 2243872 A1 | 10/2010 |
| WO | WO2017/162927 A1 | 9/2017 |

*Primary Examiner* — Mark Halpern
(74) *Attorney, Agent, or Firm* — Stites & Harbison PLLC; Richard S. Myers, Jr.

(57) ABSTRACT

There is provided a paper for packaging of medical devices comprising 5-25 wt. % (dry) synthetic fibres comprising polyester and 2.0-12.0 wt. % (dry) of a latex binder or 1.0-5.0 wt. % (dry) of a starch binder, wherein the length of the synthetic fibres is 8-14 mm and the thickness of the synthetic fibres is 5.5-9.0 dtex and wherein the paper has a grammage according to ISO 536:2012 of 70-110 g/m$^2$.

15 Claims, 15 Drawing Sheets

◇ Uncoated
□ Coated

REINFORCED PAPER FOR PACKAGING OF MEDICAL DEVICES

CROSS REFERENCE TO RELATED APPLICATIONS

This application is a § 371 National State Application of PCT/EP2019/086134 filed Dec. 18, 2019, which claims priority to EP 18248106.9 filed Dec. 27, 2018.

TECHNICAL FIELD

The present disclosure relates to the field of paper materials for packaging of medical devices.

BACKGROUND

The usage of single-use medical devices is growing. Medical devices typically need to be packed in a sterile barrier system to preserve sterility until point of use.

The transport and storage of medical devices places high demands on the robustness of the sterile barrier system used for packaging the devices. Medical device manufacturers are seeking greater security in the packaging to assure sterility and avoid product recalls due to packaging failures. The current option beyond traditional medical kraft papers of 60-80 g/m$^2$ is, when sterilisation by EtO is necessary, the synthetic material Tyvek (DuPont), which is many times more expensive than medical kraft paper.

SUMMARY

In many cases, however, it is not necessary to use a packing material that is as tough as Tyvek, which makes Tyvek over-engineered and unnecessarily expensive.

The present inventors have realized a sizeable and growing market opportunity for a reinforced paper with significantly higher strength characteristics than those of normal kraft paper.

Existing paper products for medical device packaging are not strong enough to safely package heavy or large devices. The key paper properties to improve are tear strength and Tensile Energy Absorbtion (TEA), while maintaining the permeability in the material to allow for a gas sterilization process.

There are known ways to increase either of tear strength and TEA. The problem with these known ways is however that the increase one of the strength parameters always decreases the other. A classic example of this is refining of the pulp used to make the paper, which increases TEA (and tensile strength), but decreases tear strength.

The TEA and tensile strength properties may be improved by coating or impregnation with starch, but at the expense of decreased tear strength and undesirably high paper stiffness (a reasonable level of softness/flexibility of the paper is preferred to avoid creasing in converting and handling). It has been found that the stiffness problem may be overcome by impregnating with latex instead of starch. Decreased tear strength and reduced permeability are however drawbacks of a latex impregnation. High permeability may be of particular importance when the paper material is used as a "coating base", i.e. when the converter/customer applies a layer of heat seal coating on the paper surface.

Today, the permeability issue is overcome by limiting the degree of refining of the pulp used to form the paper, which results in relatively low values for tensile strength and TEA (as discussed above).

The inventors hypothesized that the addition of fibres that are longer than the wood cellulose fibres could reinforce the paper and thus increase tear strength and TEA at the same time without unduly interfering with permeability and material softness/flexibility. Therefore, a number of different types and dimensions of such long fibres were tested.

One type of long fibres that was added by the inventors is long synthetic fibres. A general problem with long synthetic fibres is however that their bonding to the wood cellulose fibres is inferior to the bonding between wood cellulose fibres. The bonding between some synthetic fibres and wood cellulose fibres is almost non-existent. Further, the bonding between the synthetic fibres is typically weak. This means that the addition of long synthetic fibres results in increased tear strength, but decreased TEA and tensile strength. A general finding is that as the percentage of long synthetic fibres increases, the tear strength increases and the tensile strength decreases.

The present inventors found that the problem of inferior bonding (and thus the problem of the decreased TEA of the paper comprising long synthetic fibres) can be solved by coating or impregnating the paper with latex or starch.

Another finding is that the longer the synthetic fibres, the higher the tear strength. This finding is however only valid as long as the synthetic fibres are pulled out of the paper structure when tearing the paper. If the synthetic fibres are instead broken, there is no significant improvement of tear strength. It has been found that by selecting sufficiently thick synthetic fibres of the right type, such breakage may be reduced or even eliminated. Due to high strength and relatively low stiffness, polyester fibres are the preferred type of synthetic fibres.

Further, the inventors have found that there is a practical limitation to the length of the synthetic fibres, because when the fibres are longer than 14 mm, they tend to get stuck in and thus foul various parts of the paper machine.

In conclusion, the present disclosure provides a paper for packaging of medical devices comprising 5-25 wt. % (dry) synthetic fibres comprising polyester and 2.0-12.0 wt. % (dry) of a synthetic latex binder or 1.0-5.0 wt. % (dry) of a starch binder, wherein the length of the synthetic fibres is 8-14 mm and the thickness of the synthetic fibres is 4.5-9.0 dtex.

There is also provided a method of producing the paper in a paper machine, comprising the steps of adding the synthetic fibres comprising polyester to a pulp before/upstream a headbox of the paper machine, forming a paper web from the pulp and impregnating the paper web with the latex or starch binder.

DETAILED DESCRIPTION

Figure 1A:
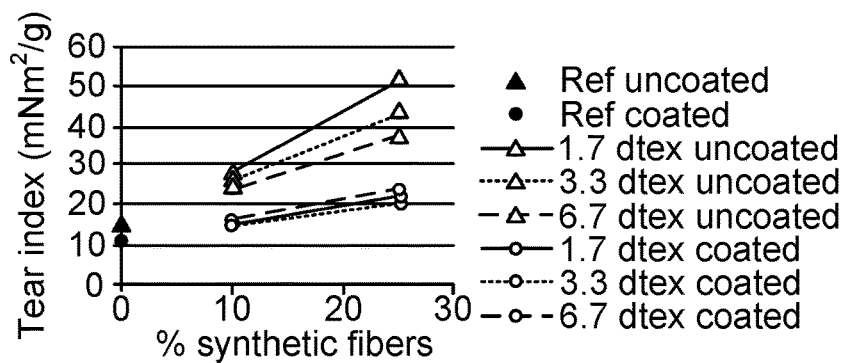
FIG. 1 shows results of the "Polyester (thickness) trial" discussed in the Examples section. The y axes in FIG. 1 show the values of various paper properties of coated and uncoated sheets to which 10% or 25% polyester fibre of different thicknesses have been added. A coated and an uncoated sheet without any polyester fibres are included as references.

As a first aspect of the present disclosure, there is thus provided a paper for packaging of medical devices. The paper is preferably a kraft paper, which means that it is mainly formed from pulp produced according to the kraft process. To achieve high strength, the kraft pulp used to form the paper preferably comprises softwood kraft pulp. In one embodiment, the kraft pulp comprises 50-100 wt. % (dry) softwood kraft pulp and 0-50 wt. % (dry) hardwood kraft pulp, such as 50-90 wt. % (dry) softwood kraft pulp and 10-50 wt. % (dry) hardwood kraft pulp In addition to cellulosic fibres (which are implicit in the term "paper"), the paper comprises 5-25 wt. % (on a dry matter basis, "dry") synthetic fibres. A preferred amount of the synthetic fibres is 8-15 wt. % (dry).

The synthetic fibres comprise polyester. It is particularly preferred that at least a sheath portion of the synthetic fibres comprises polyester. The amount of polyester in the synthetic fibres is preferably at least 50 wt. %, such as at least 90 wt. %. In one embodiment, the synthetic fibres are composed of polyester only.

Longer polyester fibres increase the tear strength more efficiently than shorter polyester fibres. At the same time, there is an increased risk of fouling the paper machine when the polyester fibres get longer. Therefore, the length of the synthetic fibres is 8-14 mm, preferably 10-14 mm and more preferably 10-12 mm.

Further, it has been found that relatively thick synthetic fibres increase tear strength more efficiently than thinner synthetic fibres. Therefore, the thickness of the synthetic fibres is 4.5-9.0 dtex, preferably 5.0-9.0 dtex and more preferably 5.5-9.0 dtex.

The synthetic fibres are preferably non-flat. Accordingly, the synthetic fibres preferably have a rounded, e.g. mainly circular or oval, cross-section.

The paper further comprises 2.0-12.0 wt. % (dry) of a synthetic latex binder or 1.0-5.0 wt. % (dry) of a starch binder. A synthetic latex binder is more preferred than a starch binder since a synthetic latex binder generally results in lower bending resistance than a starch binder. Synthetic latex binders are marketed by several companies, including Celanese, DOW, BASF and Trinseo. The synthetic latex binder may for example be an acrylic latex, such as a styrene acrylic latex or a vinyl acrylic latex. The synthetic latex binder may also be a styrene-butadiene latex.

The starch binder may for example be Perfectafilm X115 or X85 from Avebe.

It has been found that a lower amount of latex results in lower bending resistance (i.e. lower stiffness) than a higher amount of latex binder. Further, the permeability and tear index decreases with increasing amounts of latex binder, which is a reason for keeping the amount of latex binder below 12%. Accordingly, the amount of the synthetic latex binder in the paper of the first aspect is preferably 3.0-10.0 wt. % (dry), more preferably 3.0-8.0 wt. % (dry).

The grammage of the paper of the first aspect is preferably 70-110 g/m², such as 75-105 g/m², such as 75-99 g/m². Grammage is measured according to ISO 536:2012.

As discussed above, high values for TEA and tear strength are desired. As shown in the Examples section below, such high values can be achieved according to the present disclosure. Accordingly, the TEA index of the paper of the first aspect may be at least 1.5 J/g, such as 1-5-2.0 J/g, in the machine direction (MD) and at least 2.4 J/g, such as 2.4-3.4 J/g in the cross direction (CD). The geometric TEA index may be 1.9-2.5 J/g, such as 2.0-2.5 J/g. Further, the tear index of the paper of the first aspect may be at least 17.0 mNm²/g, such as 17.0-25.0 mNm²/g, in the MD and at least 21.0 mNm²/g, such 21.0-29.5 mNm²/g in the CD. TEA and tear strength is measured by ISO 1924-3:2005 and ISO 1974:2012, respectively. To obtain the TEA index, the TEA value is divided by the grammage. To obtain the tear index, the tear strength value is divided by the grammage.

As further discussed above, high permeability is a desired property. As shown in the Examples section below, high permeability can be achieved according to the present disclosure. Accordingly, the Bendtsen Porosity of the paper of the first aspect is preferably at least 250 ml/min, such as 250-800 ml/min, more preferably at least 400 ml/min, such as 400-750 ml/min. Bendtsen porosity is measured according to ISO 5636-3:2013.

As also discussed above, low stiffness is a desired property. As shown in the Examples section below, low stiffness can be achieved according to the present disclosure. Accordingly, the geometric bending resistance index of the paper of the first aspect may be 60-160 $Nm^6/kg^3$. The bending resistance is measured according to ISO 2493-1:2010 using a bending length of 10 mm and a bending angle of 15°. The geometric bending resistance is calculated as the square root of the product of the bending resistance in MD and CD:

geometric bending resistance=√(bending resistance (*MD*)\*bending resistance (*CD*)).

(The same principle applies to the calculation of the geometric TEA index.) The geometric bending resistance index is obtained by dividing the geometric bending resistance by the cube of the grammage.

The (non-indexed) geometric bending resistance of the paper of the first aspect may for example be 60-90 mN.

In one embodiment, the Cobb 60 value of at least one side, such as both sides, of the paper of the first aspect is lower than 20 g/m². A minimum Cobb 60 value may be 10 g/m². For example, the Cobb 60 value of both sides of the paper of the first aspect may in the range of 11.5-19.5 g/m². The Cobb 60 value, which represents the amount of water absorbed by a paper surface in 60 seconds, is measured according to ISO 535:2014.

As a second aspect of the present disclosure, there is provided a method producing a paper according to the first aspect in a paper machine, comprising the steps of adding the synthetic fibres comprising polyester to a pulp upstream a headbox of the paper machine, forming a paper web from the pulp and impregnating the paper web with the latex or starch binder.

In an embodiment of the second aspect, the pulp is subjected to refining before, but not after the addition of the synthetic fibres.

The impregnation may be carried out using a size press. The size press is preferably arranged at the end of a drying section of the paper machine or downstream such a drying section. The size press may also be arranged off-line, e.g. at a different geographic location. An off-line size press is however considered to be a more expensive option.

EXAMPLES

Lab Trials—Materials and Methods
Natural Fibres (Non-Wood Fibres)
Abaca, Flax and Sisal fibres were supplied by Celesa Celulosa. The natural fibres are divided into two main groups: textile and porous. Flax belongs to the textile group and the other two belong to the porous group.

Two different types of cotton linters were supplied by Celsur South. One had longer fibres (1.62 mm) than the other (1.13 mm).

The natural fibres had to be refined before addition to the pulp (see below).

Synthetic Fibres
Advansa supplied polyester fibres and a bi-component fibre:
Polyester, 1.7 dtex, 12 mm (205NSD)
Polyester, 3.3 dtex, 6 mm (157NSD)
Polyester, 3.3 dtex, 12 mm, (157NSD)
Polyester, 6.7 dtex, 12 mm (157NSD)
Bi-component fibre, 2.2 dtex, 6 mm (271P), consists of a polyethylene terephthalate (PET) core and a polyester sheath.
Goonvean supplied polyester fibres:
Polyester 2.0 dtex, 10 mm
Polyester 2.0 dtex, 8 mm
Polyester 1.7 dtex, 6 mm
Polyester 1.7 dtex, 12 mm
Fibervision supplied a bi-component fibre:
Bi-component fibre, 1.7 dtex, 4 mm, consists of a polypropylene (PP) core and polyethylene (PE) sheath.
Eastman supplied polyester fibres (Cyphrex 10101) that are flat and relatively short (1.5 mm). The thickness is 2.5 µm and the width is 18 µm.
Carboxymethyl Cellulose (CMC)
Mare supplied a type of CMC called Niklacell UV70. It was used for the CMC-treated polyester fibre (see below).
Pulp
A mixture six parts of softwood and three parts of hardwood (eucalyptus) was used. The softwood was Södra's Green T quality and the hardwood pulp was supplied by Navia. The pulp mixture was refined at MoRe Research prior to the sheeting (see Refining below).
Wet End Chemicals
The following wet end chemicals were used: cationic starch and cationic wet strength agent.
In the trial with CMC-treated polyester fibre, the following chemicals were also used:
Alum
Nalco 1044 (cationic polyacrylamide, "C-PAM") supplied by Nalco
Coating Materials/Binders
The following coatings were used (applied in a lab size press equipment):
Vinacryl 4333, latex, supplied by Celanese
Primal NW-1845 K, styrene acrylic latex, supplied by DOW
Primal E-941 P, hydrophobic styrene acrylic latex, supplied by DOW
Acronal LA 471 S, aqueous dispersion of a heat-cross-linking acrylic ester copolymer, produced with acrylonitrile, supplied by BASF
Acronal S505, aqueous dispersions of acrylic ester and styrene copolymers, supplied by BASF
Styronal D 517, aqueous dispersions of styrene-butadiene copolymer, supplied by BASF
Eastek 1100, film-forming polyester polymer supplied as an aqueous dispersion containing 33% polymer solids, supplied by Eastman
Eastek 1200, a polymer dispersion that is a film forming polyester polymer supplied as an aqueous solution containing 2% n-propanol and 30% polymer solids, supplied by Eastman
TRINSEO XZ96821.00, latex, supplied by Trinseo
Modified starch, 5% solids, supplied by Avebe
POVAL 28-99, PVOH (fully saponified grade), 5% solids, supplied by Kuraray
Refining
Dried unrefined pulp was sent as A4 sheets to MoRe Research in Örnsköldsvik, Sweden. Six parts of the softwood pulp and three parts of hardwood pulp were co-refined in an Escher Wyss conical refiner (PFI type) at MoRe with total energy input of 65 kWh/ton and with a medium edge load. Refining was carried out at a concentration of about 3%.

After refining the pulp was dewatered to a concentration of 30%.

The natural fibres (Abaca, Sisal, Flax and Cotton linters (both lengths)) were refined to approximately the same refining level as the cellulose pulp, which had a Schopper Riegler (SR) number of 17.3 after PFI refining (see table 1). The sisal pulp was however not refined as it had an SR number of 43. The synthetic fibres were not refined since refining was not expected to have any effect on such fibres.

TABLE 1

| Pulp | SR before PFI | SR after PFI |
| --- | --- | --- |
| Reference (Navia Eucalyptus + Södra Green T) | | 17.3 |
| Abaca | 14.3 | 18.5 |
| Sisal | 43.1 | — |
| Flax | 13.0 | 18.5 |
| Cotton linters long | 13.8 | 18.7 |
| Cotton linters short | 12.3 | 19.0 |

Introduction to the Lab Trials

It has been found that the addition of synthetic fibres impairs the tensile strength of the paper, probably because the number of hydrogen bonds in the paper is reduced. It was hypothesized that coating the paper with a binder would not only compensate for this loss, but also make the paper stronger than a paper without synthetic fibres. Further, it had been found that tear strength increases with the addition of synthetic fibres and decreases when a binder coating is applied. Still, it was hypothesized that it would be possible to achieve a net positive effect.

A trial to evaluate how polyester fibres of the same length, but different thicknesses influenced the paper properties was performed. Also a trial with five different natural fibres was conducted to investigate the effect on the paper properties.

Synthetic fibres appear to have poor ability to bind to the cellulose fibres. It was tested if a stronger paper may be created by providing links between the fibres (synthetic and cellulose). Bi-component fibres consist of two layers and if a paper comprising such fibres is heat treated the outer layer of the bi-component fibre can melt and possibly create the supporting link. The linkage between synthetic fibres and cellulose could also be achieved by coating with a binder.

Polyester fibres treated with alum and CMC had been reported to achieve better adhesion to the cellulose fibres. This concept was tested in the CMC polyester trial (see below).

A trial to evaluate if Eastman's flat and relatively short polyester fibres treated with a binder could increase strength in paper was also performed (see below).

Lab Method

In all lab trials the following base method was used (in some cases with some modifications, see below).

Sheets with conditioned grammage aiming for 70 g/m² (uncoated) were produced in a Finnish sheet former, pressed and dried restrained in a climate room (50% humidity and 23° C.).

Cationic starch and cationic wet strength agent were added to the pulp as these chemical additives are normally included in medical papers. The synthetic fibres were considered "dead" material and the dosage of chemical additives was therefore calculated on the cellulosic pulp only. For the avoidance of doubt, the natural fibres were not considered to be "dead" material.

The synthetic fibres were weighed and put in small cans. Water was added to the cans which were then closed and shaken.

The reaction time for starch was 120 seconds and for the wet strength agent it was 30 seconds. pH was adjusted to 7 with sodium hydroxide or sulfuric acid. The sheets were coated using a lab size press.

Paper Testing

The following methods were used for paper testing:
Burst strength was measured using a method based on the standard ISO 2758.
Tear strength was measured using a method based on the standard ISO 1974.
Tensile energy absorption (TEA) was measured using a method based on the standard ISO1924-3.
Tensile strength was measured using a method based on the standard ISO1924-3.
Stretchability was measured using a method based on the standard ISO1924-3.
Bending resistance was measured using a method based on the standard ISO 2493-1.
Air permeability was measured using a method based on the standards ISO 5636-3 and ISO 5636-5.

Description of Lab Trials

Polyester (Thickness) Trial

In the polyester (thickness) trial, polyester fibres of different thicknesses were added to evaluate how the strength properties were affected. Since it previously had been found that synthetic fibres increases tear strength, but decrease other strength parameters, sheets were tested with and without coating with a binder. As explained above, it was hypothesized that the coating could act as a link between the synthetic fibres and the cellulose fibres and thereby increase strength (burst, tensile, tear). Three different polyester fibres having the same length, but different thicknesses were tested, see table 2.

TABLE 2

In each case, the amount of starch and wet strength agent was 0.5% and 1.3% (based on the amount of pulp), respectively. The binder for the coating was Vinacryl 4333.

| No | Pulp (%) | Reinforcing fibre (%) | Reinforcing fibre (type) |
| --- | --- | --- | --- |
| 1 (ref) | 100 | 0 | |
| 2 | 90 | 10 | Polyester, 1.7 dtex, 12 mm (Advansa) |
| 3 | 75 | 25 | Polyester, 1.7 dtex, 12 mm (Advansa) |
| 4 | 90 | 10 | Polyester, 3.3 dtex, 12 mm (Advansa) |
| 5 | 75 | 25 | Polyester, 3.3 dtex, 12 mm (Advansa) |
| 6 | 90 | 10 | Polyester, 6.7 dtex, 12 mm (Advansa) |
| 7 | 75 | 25 | Polyester, 6.7 dtex, 12 mm (Advansa) |

Natural Fibres Trial

Different kinds of natural fibres were added to evaluate how strength properties and other properties like permeability, stretch and bending resistance was affected, see table 3. For the natural fibres trial, frames for restrained drying were not available. Instead, sheets were dried on "Perstorp plates". The sheets were stamped in wet condition and after drying, the stamps were measured to determine if the sheets had shrunken or not. According to the measurements, the sheets in the natural fibres trial had not shrunken during drying.

TABLE 3

In each case, the amount of starch and wet strength agent was 0.5% and 1.3% (based on the amount of pulp), respectively. Both coated and uncoated samples were prepared. The binder for the coated samples was Vinacryl 4333.

| No | Pulp (%) | Reinforcing fibre (%) | Reinforcing fibre (type) |
|---|---|---|---|
| 1 (ref) | 100 | 0 | — |
| 2 | 90 | 10 | Abaca |
| 3 | 75 | 25 | Abaca |
| 4 | 0 | 100 | Abaca |
| 5 | 90 | 10 | Flax |
| 6 | 75 | 25 | Flax |
| 7 | 0 | 100 | Flax |
| 8 | 90 | 10 | Sisal |
| 9 | 75 | 25 | Sisal |
| 10 | 0 | 100 | Sisal |
| 11 | 90 | 10 | Cotton linters (long) |
| 12 | 75 | 25 | Cotton linters (long) |
| 13 | 0 | 100 | Cotton linters (long) |
| 14 | 90 | 10 | Cotton linters (short) |
| 15 | 75 | 25 | Cotton linters (short) |
| 16 | 0 | 100 | Cotton linters (short) |

Bi-Component Fibre Trial

In the bi-component fibres, the sheath has a lower melting point than the core. In this trial, dry sheets containing bi-component fibres were put between two metal plates having a temperature of about 175° C. for a time period of 40 seconds to test if increased strength can be obtained by links formed between the melted polymer of the sheath and cellulose fibres (see table 4). Sheets were pressed using two different pressures to see if it was possible to achieve higher strength by pressing (see table 4).

TABLE 4

In these trials, bi-component fibres are used as the reinforcing fibre. In each case, the amount of starch and wet strength agent was 0.5% and 1.3% (based on the amount of pulp), respectively. The binder for the coating was Vinacryl 4333.

| No | Pulp (%) | Reinforcing fibre (%) | Reinforcing fibre (type) | Heating time (s) | Pressure (kPa) |
|---|---|---|---|---|---|
| 1 (ref) | 100 | 0 | — | 40 | 400 |
| 2 | 90 | 10 | Fibervision, 1.7 dtex, 4 mm | 40 | 400 |
| 3 | 75 | 25 | Fibervision, 1.7 dtex, 4 mm | 40 | 400 |
| 4 | 75 | 25 | Fibervision, 1.7 dtex, 4 mm | 40 | 600 |
| 5 | 90 | 10 | Advansa 2.2 dtex, 6 mm | 40 | 400 |
| 6 | 75 | 25 | Advansa 2.2 dtex, 6 mm | 40 | 400 |

CMC-Treated Polyester Trial

The 12 mm long and 3.3 dtex thick polyester fibre from Advansa was used. To an aqueous solution of the polyester, alum and CMC were added in an amount of 0.7% and 1.6% (based on the amount of polyester fibre), respectively. The CMC-treated polyester solution was thereafter added to the pulp mixture at a concentration 0.5% to prepare sheets comprising different amounts of the polyester fibre. For all samples except one, the pH was the same as in the other trials, i.e. 7. In the other sample, the pH was adjusted to 5.

Starch, wet strength agent and C-PAM were also added to the pulp. The dosages of starch and wet strength agent were the same as in the other trials, i.e. 0.5% and 1.3%, respectively. The C-PAM dosage was 0.04%. C-PAM was excluded in one sample to evaluate its effects. The CMC-treated polyester trial is summarized in table 5.

TABLE 5

The binder for the coating was Vinacryl 4333.

| No | Pulp (%) | Reinforcing fibre (%) | C-PAM (%) | pH |
|---|---|---|---|---|
| 1 (ref) | 100 | 0 | 0.4 | 7 |
| 2 | 94.4 | 5.6 | 0.4 | 7 |
| 3 | 90 | 10 | 0.4 | 7 |
| 4 | 90 | 10 | 0.4 | 5 |
| 5 | 90 | 10 | 0 | 7 |
| 6 | 75 | 25 | 0.4 | 7 |

Flat and Short Fibre Trial

In this trial, the flat and short fibre from Eastman (Cyphrex 10101) was used together with the binders supplied by Eastman. The flat and short fibres were dispersed to a consistency of 1% and mixed in a pulp disintegrator for one minute. Longer and round polyester fibres from Advansa (3.3 dtex, 12 mm) were included in the trial for reference sheets.

The sheets comprising the flat and short fibres were heat-dried at 140° C. The sheets comprising the polyester fibre from Advansa were dried at room temperature as in the other trials. A reference to each sample was made, one dried in 150° C. and one dried in room temperature.

The sheets were coated with either Eastek 1100 or Eastek 1200. The coated sheets were dried in an oven at 150° C. A sheet coated with the Eastek 1200 binder was also dried in room temperature as comparison. The flat and short fibre trial is summarized in table 6.

TABLE 6

In each case, the amount of starch and wet strength agent was 0.5% and 1.3% (based on the amount of pulp), respectively. All sheet dryings were carried out on a "Perstorp plate".

| No | Pulp (%) | Reinforcing fibre (%) | Reinforcing fibre (type) | Sheet drying temp. (° C.) | Coating (type) | Coated sheet drying temp. (° C.) |
|---|---|---|---|---|---|---|
| 1A (ref) | 100 | 0 | | Room temp. | Eastek 1200 | Room temp. |
| 1B (ref) | 100 | 0 | | Room temp. | Eastek 1100 | 150 |
| 1C (ref) | 100 | 0 | | Room temp. | Eastek 1200 | 150 |
| 2A (ref) | 100 | 0 | | 140 | Eastek 1200 | Room temp. |
| 2B (ref) | 100 | 0 | | 140 | Eastek 1100 | 150 |
| 2C (ref) | 100 | 0 | | 140 | Eastek 1200 | 150 |
| 3A | 90 | 10 | Flat and short | 140 | Eastek 1200 | Room temp. |
| 3B | 90 | 10 | Flat and short | 140 | Eastek 1100 | 150 |
| 3C | 90 | 10 | Flat and short | 140 | Eastek 1200 | 150 |
| 4A | 75 | 25 | Flat and short | 140 | Eastek 1200 | Room temp. |
| 4B | 75 | 25 | Flat and short | 140 | Eastek 1100 | 150 |
| 4C | 75 | 25 | Flat and short | 140 | Eastek 1200 | 150 |
| 5A | 90 | 10 | Longer and round | Room temp. | Eastek 1200 | Room temp. |
| 5B | 90 | 10 | Longer and round | Room temp. | Eastek 1100 | 150 |
| 5C | 90 | 10 | Longer and round | Room temp. | Eastek 1200 | 150 |
| 6A | 75 | 25 | Longer and round | Room temp. | Eastek 1200 | Room temp. |

TABLE 6-continued

In each case, the amount of starch and wet strength agent was 0.5% and 1.3% (based on the amount of pulp), respectively. All sheet dryings were carried out on a "Perstorp plate".

| No | Pulp (%) | Reinforcing fibre (%) | Reinforcing fibre (type) | Sheet drying temp. (° C.) | Coating (type) | Coated sheet drying temp. (° C.) |
|---|---|---|---|---|---|---|
| 6B | 75 | 25 | Longer and round | Room temp. | Eastek 1100 | 150 |
| 6C | 75 | 25 | Longer and round | Room temp. | Eastek 1200 | 150 |

Refining and Fibre Length Trial

The softwood/hardwood pulp mixture described above was refined as described above, but at different energy levels: 65 kW/h (as above), 85 kW/h and 105 kWh/ton. Further, polyester fibres of two different lengths, 6 mm and 12 mm, were tested. Sheets without any polyester fibres were prepared as references (see table 7).

TABLE 7

In each case, the amount of starch and wet strength agent was 0.5% and 1.3% (based on the amount of pulp), respectively. The Advansa polyester fibres having the thickness 3.3 dtex were used. All sheets were coated with the Vinacryl 4333 latex.

| No | Pulp (%) | Reinforcing fibre (%) | Reinforcing fibre length (mm) | Refining level (kWh/t) |
|---|---|---|---|---|
| 1 (ref) | 100 | 0 | | 65 |
| 2 (ref) | 100 | 0 | | 85 |
| 3 (ref) | 100 | 0 | | 105 |
| 4 | 83 | 17 | 12 | 65 |
| 5 | 83 | 17 | 12 | 85 |
| 6 | 83 | 17 | 12 | 105 |
| 7 | 83 | 17 | 6 | 65 |
| 8 | 83 | 17 | 6 | 85 |
| 9 | 83 | 17 | 6 | 105 |

Starch, Wet Strength Agent and A-PAM Trial

In this trial, the impact of increased amounts of starch and wet end chemicals were tested. Further, the impact of adding anionic polyacrylamide (A-PAM) was tested (see table 8)

TABLE 8

In each case, the 12 mm and 3.3 dtex Advansa polyester fibre was added in an amount of 17%. The Advansa polyester fibres having the thickness 3.3 dtex were used. All sheets were coated with the Vinacryl 4333 latex.

| No | Starch (% or pulp) | Wet strength agent (% of pulp) | A-PAM (% of pulp) |
|---|---|---|---|
| 1 (ref) | 0.5 | 1.3 | 0 |
| 2 | 1.6 | 2.6 | 0.5 |
| 3 | 1.6 | 1.3 | 0 |

Binder Type Trial

Sheets reinforced with 17% Advansa polyester fibre (12 mm, 3.3 dtex) were coated with different binders, see table 9. All the latex coatings were diluted to two times their original volumes.

TABLE 9

In each case, the amount of starch and wet strength agent was 0.5% and 1.3% (based on the amount of pulp), respectively.

| No | Coating | Coating type | Other |
|---|---|---|---|
| 1 | Vinacryl 4333 | latex | 2x dilution |
| 2 | Primal NW-1845 K | latex | 2x dilution |
| 3 | Primal E-941 P | latex | 2x dilution |
| 4 | Acronal S 505 | latex | 2x dilution |
| 5 | TRINSEO XZ96821.00 | latex | 2x dilution |
| 6 | Avebe PR1507B | starch | 5% solids content |
| 7 | POVAL 28-99 | PVOH | 5% solids content |

Length and Thickness Trial

In this trial, the lengths and thicknesses of reinforcing polyester fibres were varied. The sheets were coated with either latex (TRINSEO XZ96821.00) in a concentration of 20% or a mixture of latex (in a concentration of 10%) and starch (in a concentration of 4%), see table 10.

TABLE 10

In each case, the amount of starch and wet strength agent was 0.5% and 1.3% (based on the amount of pulp), respectively. Polyester fibres were used as reinforcing fibres.

| No | Pulp (%) | Reinforcing fibre (%) | Reinforcing fibre thickness and length | Coating |
|---|---|---|---|---|
| 1 L | 85 | 15 | 2.0 dtex, 10 mm | latex |
| 1 C | 85 | 15 | 2.0 dtex, 10 mm | latex + starch |
| 2 L | 85 | 15 | 2.0 dtex, 8 mm | latex |
| 2 C | 85 | 15 | 2.0 dtex, 8 mm | latex + starch |
| 3 L | 85 | 15 | 1.7 dtex, 6 mm | latex |
| 3 C | 85 | 15 | 1.7 dtex, 6 mm | latex + starch |
| 4 L | 85 | 15 | 6.7 dtex, 6 mm | latex |
| 4 C | 85 | 15 | 6.7 dtex, 6 mm | latex + starch |
| 5 L | 85 | 15 | 1.7 dtex, 12 mm | latex |
| 5 C | 85 | 15 | 1.7 dtex, 12 mm | latex + starch |
| 6 L | 85 | 15 | 6.7 dtex, 12 mm | latex |
| 6 C | 85 | 15 | 6.7 dtex, 12 mm | latex + starch |
| 7 L | 85 | 15 | 50% 3.3 dtex, 6 mm + 50% 3.3 dtex, 12 mm | latex |
| 7 C | 85 | 15 | 50% 3.3 dtex, 6 mm + 50% 3.3 dtex, 12 mm | latex + starch |
| 8 L | 85 | 15 | 50% 6.7 dtex, 12 mm + 50% 1.7 dtex, 12 mm | latex |
| 8 C | 85 | 15 | 50% 6.7 dtex, 12 mm + 50% 1.7 dtex, 12 mm | latex + starch |

Air Resistance Trial

In this trial, the effect on air resistance of the addition of polyester fibres and coating with a binder was evaluated. An uncoated sheet without polyester fibres and an uncoated sheet with 15% polyester fibre (6.7 dtex, 12 mm) were included as references. The other sheets tested were numbers 6 L and 6 C from table 10. Sheets corresponding to 6 L and 6 C, but without synthetic fibres, were also included as references.

Description of Paper Machine Trial

A full scale trial was carried out on a paper machine.

A pulp mixture comprising six parts by weight of softwood kraft pulp (market pulp), four parts by weight of hardwood kraft pulp (market pulp) and 10 wt. % polyester fibre (6.7 dtex, 12 mm, Advansa) as well as 0.5% cationic starch, 1.5% cationic wet strength agent and 0.5% was provided. Before adding the polyester fibres, the pulp was subjected to low consistency refining (65 kWh/ton, disc refiner). In the headbox, the consistency of the diluted pulp mixture was about 0.4%. A paper web was formed on a wire section. The paper web was dewatered in a press section.

The dewatered paper web was then dried in a subsequent drying section. In a size press, the dried paper web was coated/impregnated with a latex binder (TRINSEO XZ96821.00) composition having a solids content of 15 wt. % in an amount of about 5.3 g/m² (dry). The proportion of latex binder (based on the dry weight of the final product) was thus about 6.0% given that the grammage (dry) of the final product was 88.7 g/m².

Results of Lab Trials

Polyester (Thickness) Trial

The average grammage of uncoated and coated sheets was 72.4 g/m² and 88.2 g/m², respectively.

Results of the polyester trials are shown in FIG. 1. FIG. 1A shows that addition of polyester fibres increase the tear index. A higher amount of fibres resulted in a greater increase. Interestingly, the thinnest (1.7 dtex) fibres had the greatest effect on tear index in the paper sheets that were not coated with a binder, while the thickest (6.7 dtex) fibres had the greatest effect on tear index in the paper sheets that were coated with a binder.

Figure 1B:
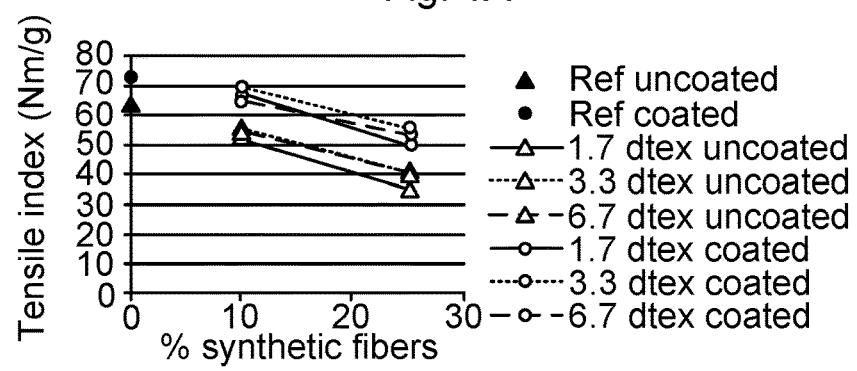

FIG. 1B shows that addition of polyester fibres decrease the tensile index. A higher amount of fibres resulted in a greater decrease. It is however notable that coating with the binder increased tensile index in all cases. The increase was higher for the paper sheets comprising polyester fibres than for the reference sheets. The coated paper sheets comprising 10% polyester fibres actually had a higher tensile index than the uncoated reference sheet.

Figure 1C:
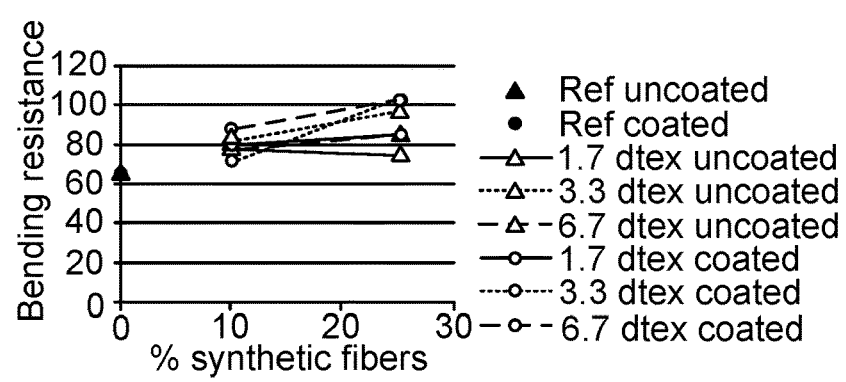
Figure 1D:
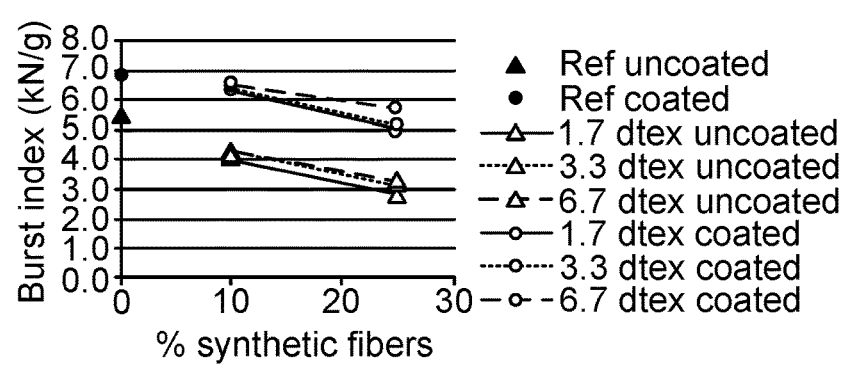
Figure 1D:
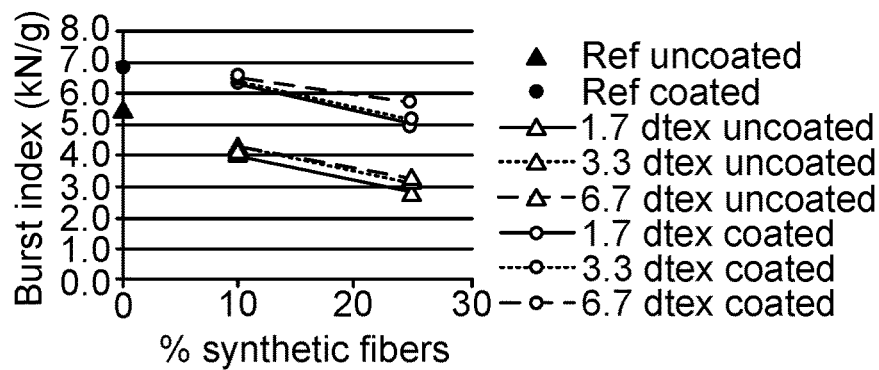

FIG. 1C shows that the bending resistance was increased by the addition of polyester fibres.

Figure 1E:
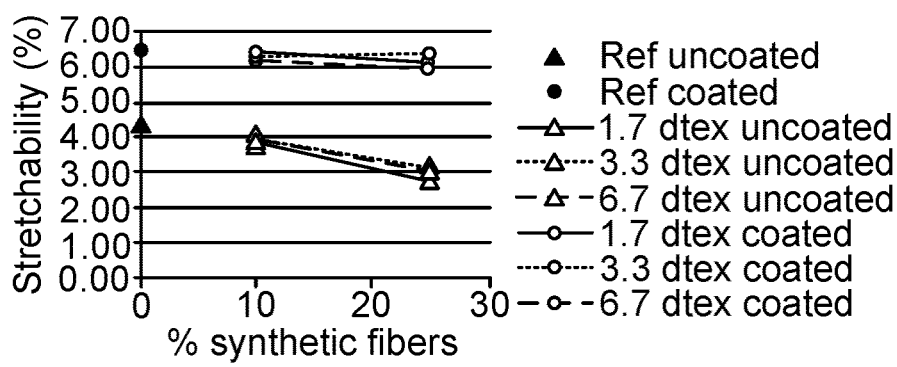

FIG. 1E shows that coating the paper sheets with the binder significantly increases the stretchability. Further, the stretchability of the coated paper sheets is more or less unaffected by the addition of polyester fibres. In contrast, the addition of polyester fibres decreases the stretchability of uncoated sheets.

Figure 1F:
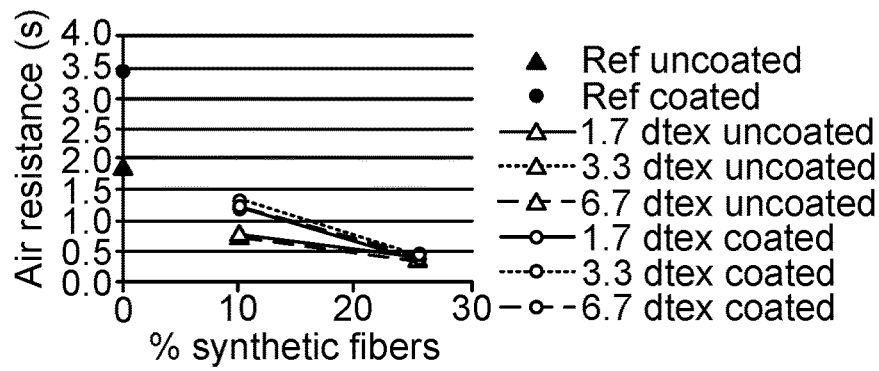

FIG. 1F shows that coating of the paper sheet with the binder significantly decreased the permeability (i.e. increased the air resistance). However, the addition of the polyester fibres increased the permeability (i.e. decreased the air resistance). For the sheet comprising polyester fibres, the effect of the coating on the permeability was acceptable. When the amount of polyester fibres in the sheets was 25%, the coating had no negative effect on the permeability. It is also notable that all coated sheets comprising polyester fibres showed significantly higher permeability than the uncoated reference sheet comprising no polyester fibres.

Natural Fibres Trial

The average grammage of the uncoated and coated sheets was 80.5 g/m² and 94.2 g/m², respectively.

The largest effects of the natural (non-wood) fibres on paper properties were seen in sheets containing only (100%) the natural fibres. Such sheets are however not a realistic alternative.

Figure 2A:
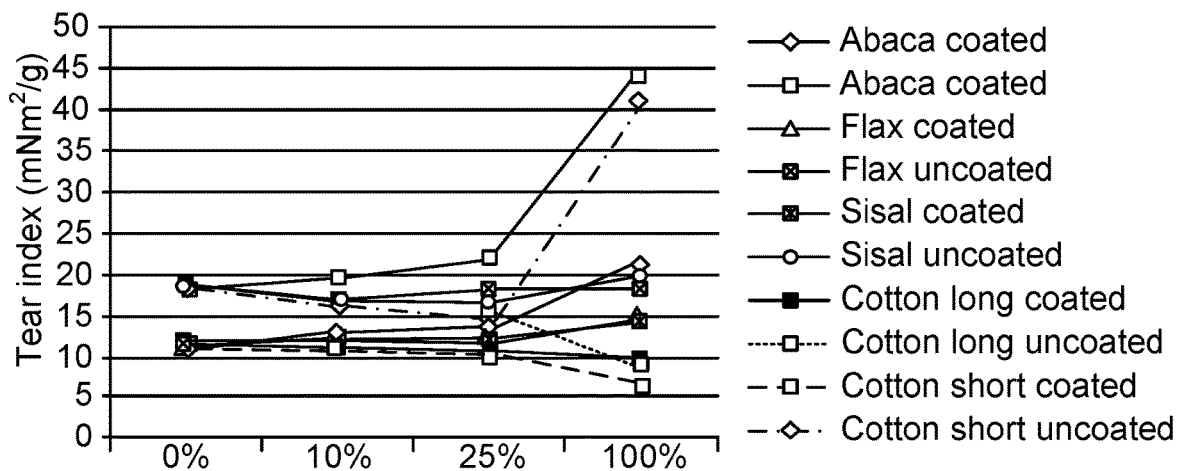
FIG. 2 shows results of the "Natural fibres trial" discussed in the Examples section. The y axes in FIG. 2 show the values of various paper properties of coated and uncoated sheets to which different kinds of natural fibres have been added in an amount of 10% or 25%. Coated and an uncoated sheets without any polyester fibres or without any cellulose fibres ("100%") are included as references.
Figure 2B:
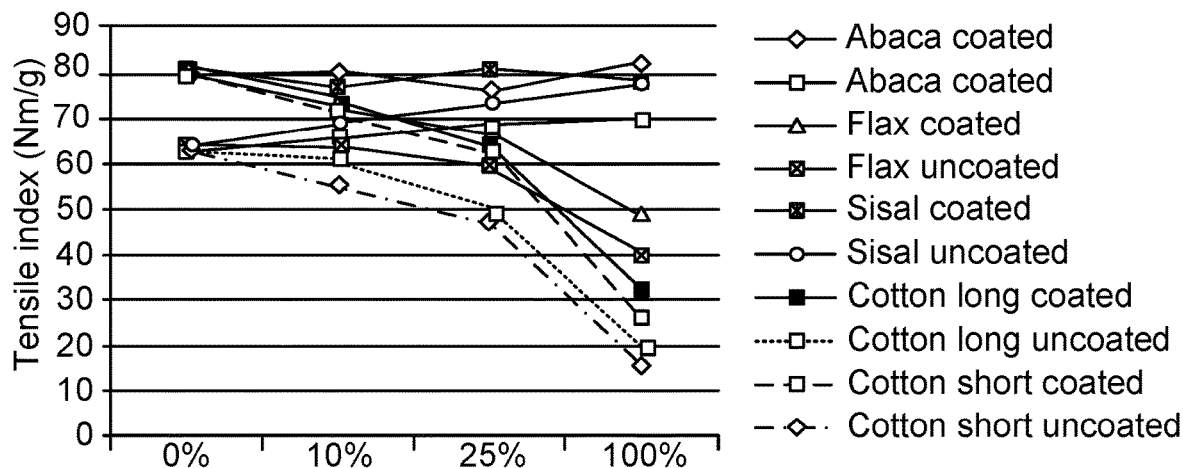
Figure 2C:
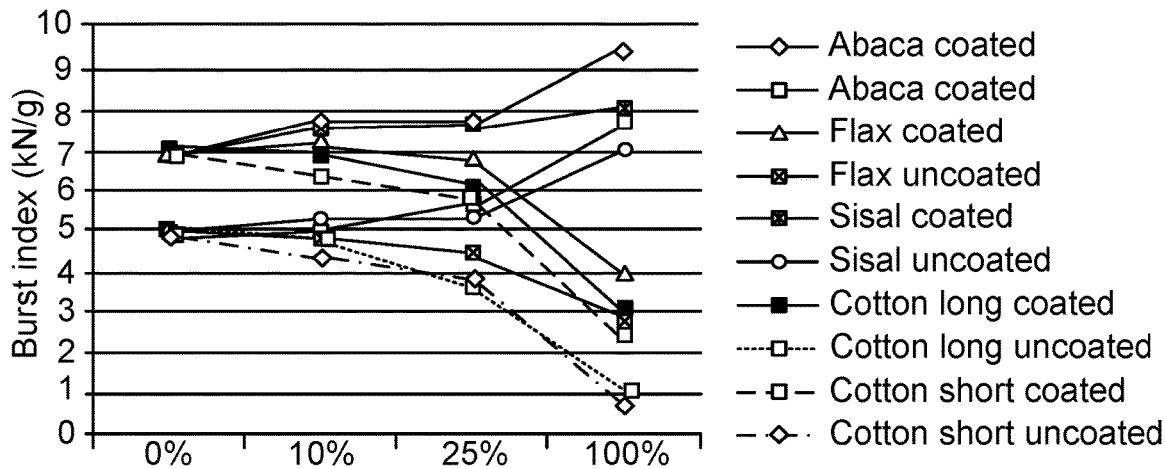
Figure 2D:
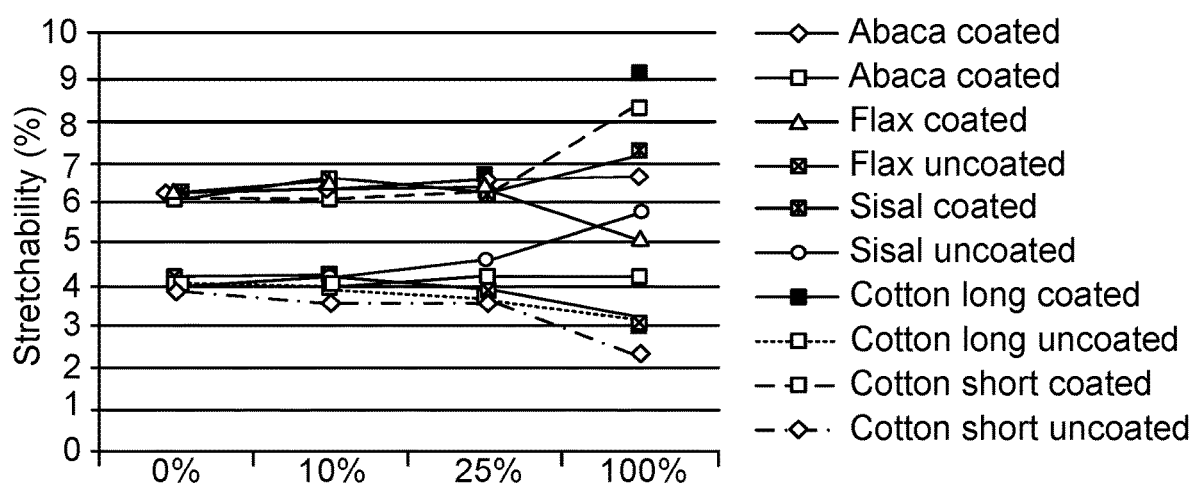

None of the coated sheets comprising 10% or 25% natural (non-wood) fibres was able to reach the same tear index as the uncoated reference sheet comprising no natural (non-wood) fibres (see FIG. 2A). For the uncoated sheets, the Abaca fibres were the only fibres that increased the tear index when added in an amount below 100% (i.e. 10% or 25%) (see FIG. 2A). However, the uncoated sheet comprising 10% or 25% Abaca fibres only showed a slight increase in tensile index (FIG. 2B) on no increase in stretchability (FIG. 2D). It was thus concluded that addition of the natural (non-wood) fibres could not increase both tensile index and TEA index at the same time, not even after coating with the binder.

Bi-Component Fibre Trial

Figure 3A:
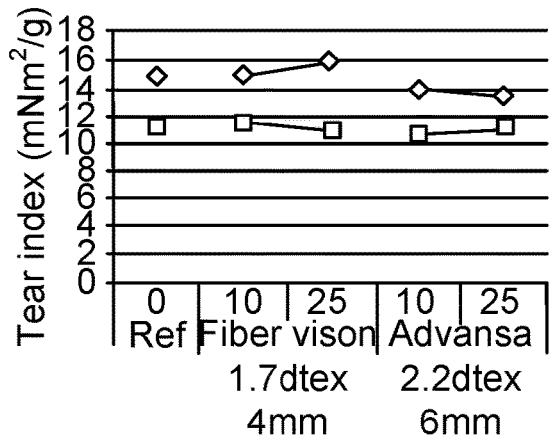
FIG. 3 shows results of the "Bi-component fibre trial" discussed in the Examples section. The y axes in FIGS. 3A-F show the values of various paper properties of coated and uncoated sheets to which 10% or 25% bi-component fibre of two different types have been added. A coated and an uncoated sheet without any bi-component fibres are included as references.
In FIGS. 3G-J, two different pressures are compared for coated and uncoated sheets comprising 25% bi-component fibre.
Figure 3D:
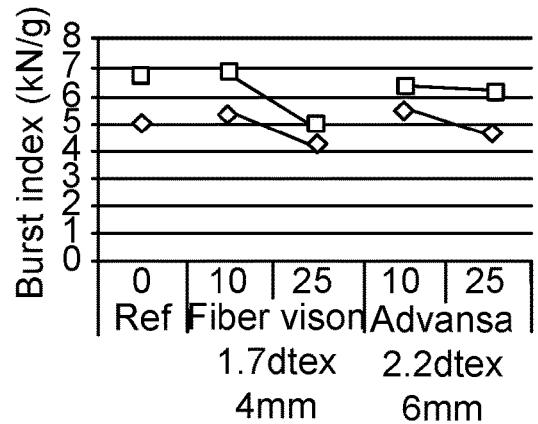
Figure 3B:
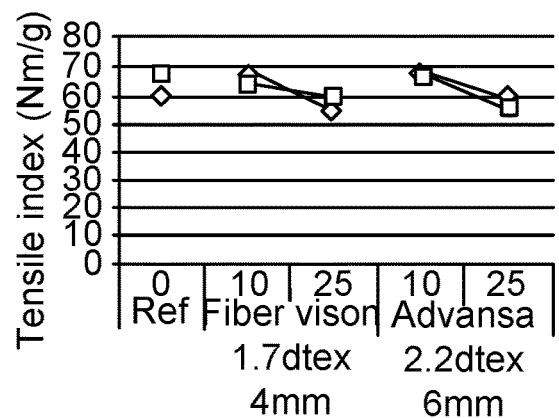
Figure 3E:
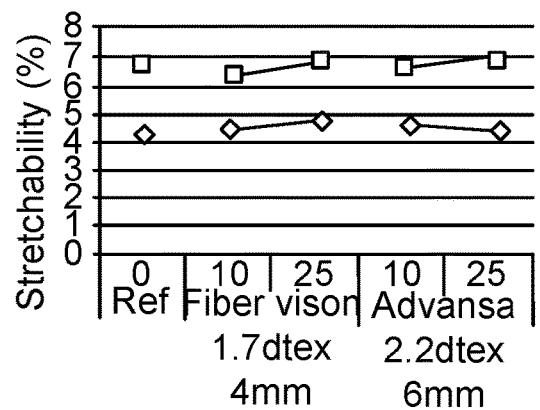
Figure 3C:
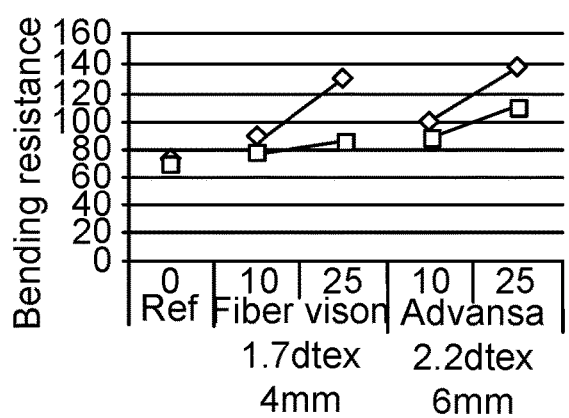
Figure 3F:
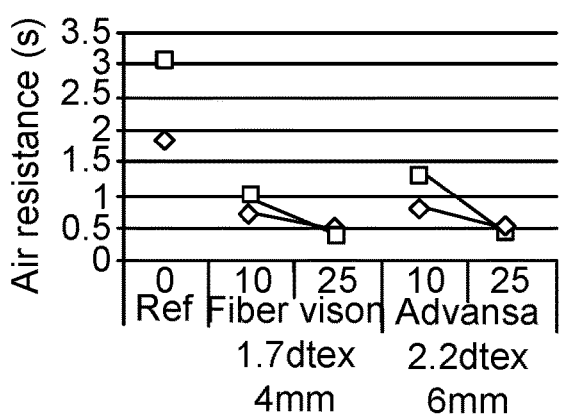
Figure 3G:
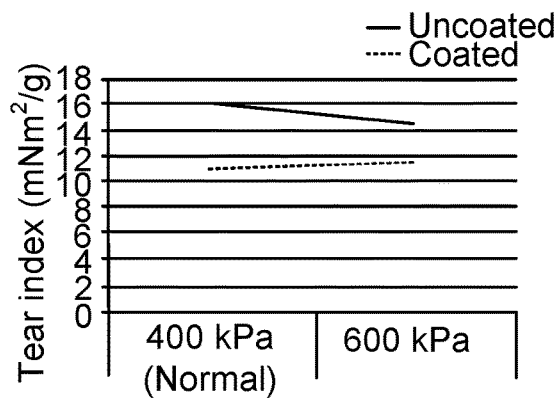
Figure 3I:
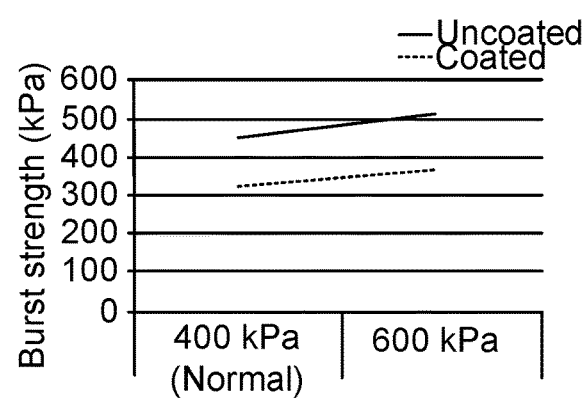
Figure 3H:
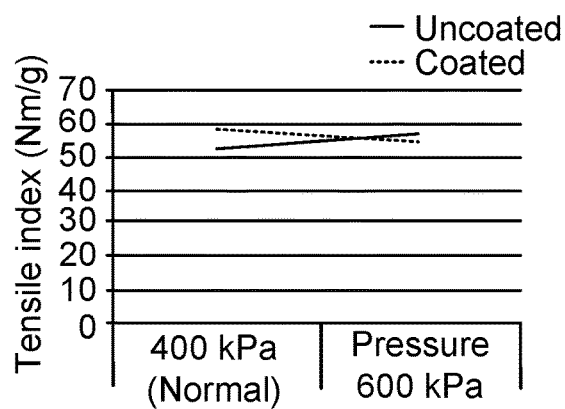
Figure 3J:
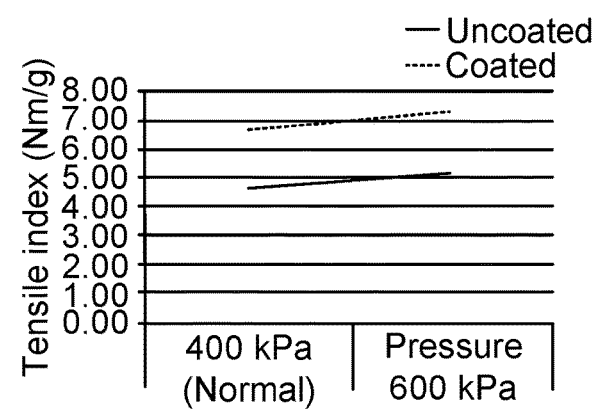

FIG. 3A shows that the uncoated sheet comprising 25% of the Fibervision fibres (1.7 dtex, 4 mm) and prepared using a pressure of 400 kPa was the only sheet of the trial showing a higher tear index than the uncoated reference sheet. The difference compared to the reference sheet is however modest. Further, the effect adding the Fibervision fibre in an amount of 25% on tensile strength was negative (FIG. 3B) and the effect on stretchability was insignificant (FIG. 3D). No significant improvements were obtained by increasing the pressure to 600 kPa (Figures G-J). It was therefore decided not to proceed with the bi-component fibres.

CMC-Treated Polyester Trial

Figure 4A:
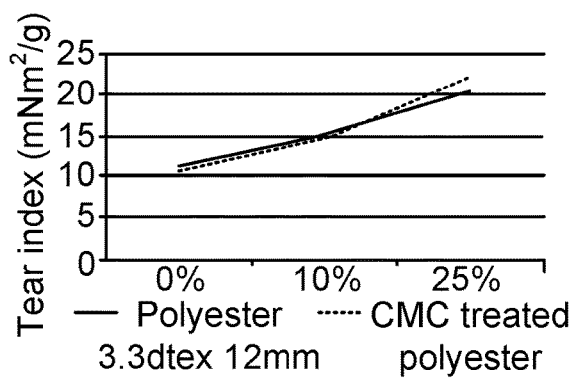
FIG. 4 shows results of the "CMC-treated polyester trial" discussed in the Examples section. The y axes in FIG. 4 show the values of various paper properties of sheets to which CMC-treated polyester fibre has been added in an amount of 10% or 25%. Values for corresponding sheets that have not been treated with CMC are also shown. Sheets without polyester fibres are included as references.
Figure 4C:
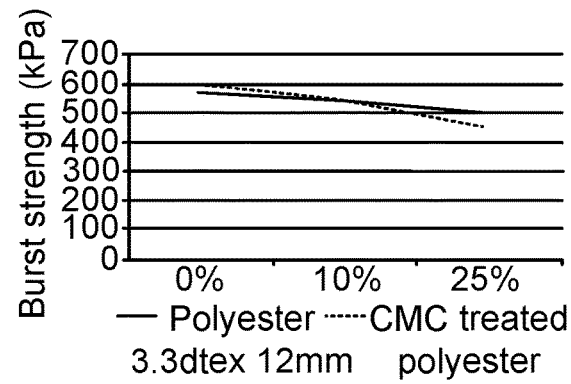
Figure 4B:
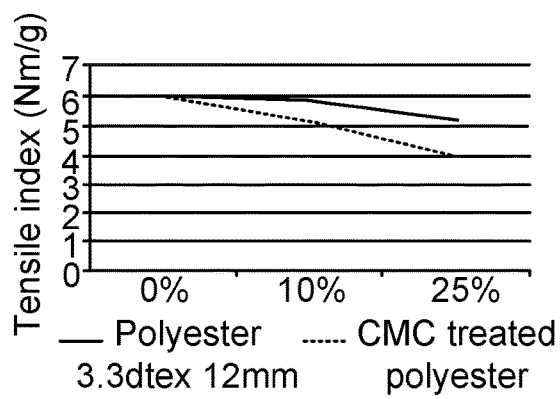
Figure 4D:
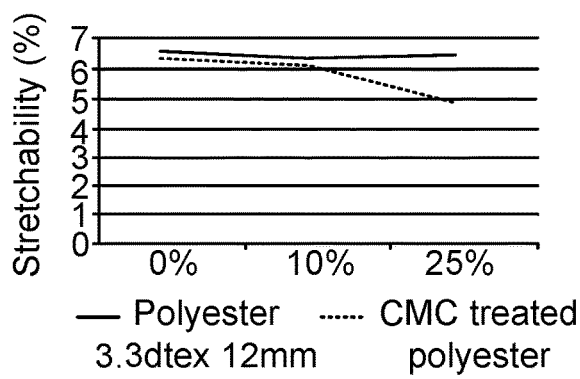

FIG. 4A shows that the CMC-treated polyester fibre increases the tear index to about the same degree as the non-treated polyester fibre of the same type (included as a reference). However, the CMC-treated fibre has a more detrimental effect on tensile index and stretchability than the reference fibre.

The decrease in pH from 7 to 5 had no significant effect, neither had the addition of C-PAM.

Flat and Short Fibre Trial

Figure 5A:
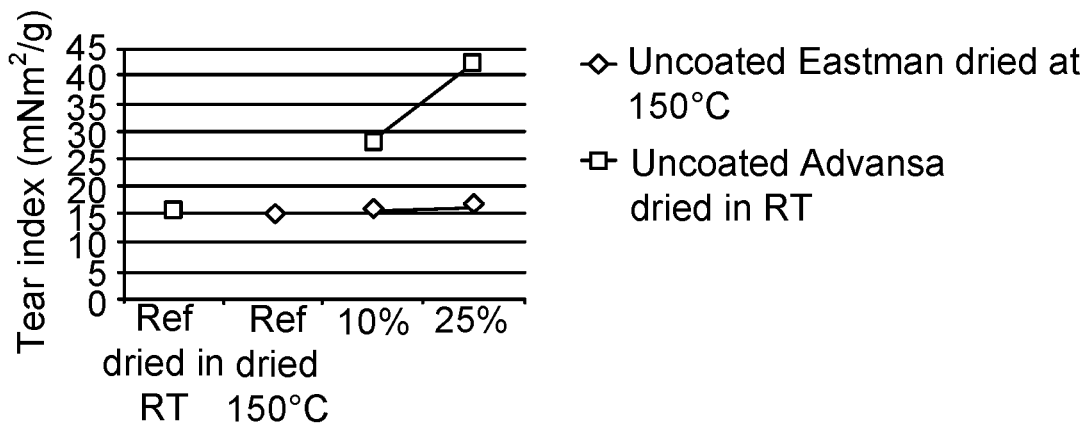
FIG. 5 shows results of the "Flat and short fibre trial" discussed in the Examples section. The y axes in figures 5A-D show the values of various paper properties of uncoated sheets to which 10% or 25% of the flat and short fibre has been added. An uncoated sheet without any added fibre is included as a reference. Further, uncoated sheets to which longer and round polyester fibre has been added are included as references. The y axes in figures 5E-H show the values of various paper properties of coated sheets to which 10% or 25% of the flat and short fibre has been added. Coated sheets without any added fibres are included as a reference. Further, coated sheets to which longer and round polyester fibre has been added are included as a reference.
Figure 5B:
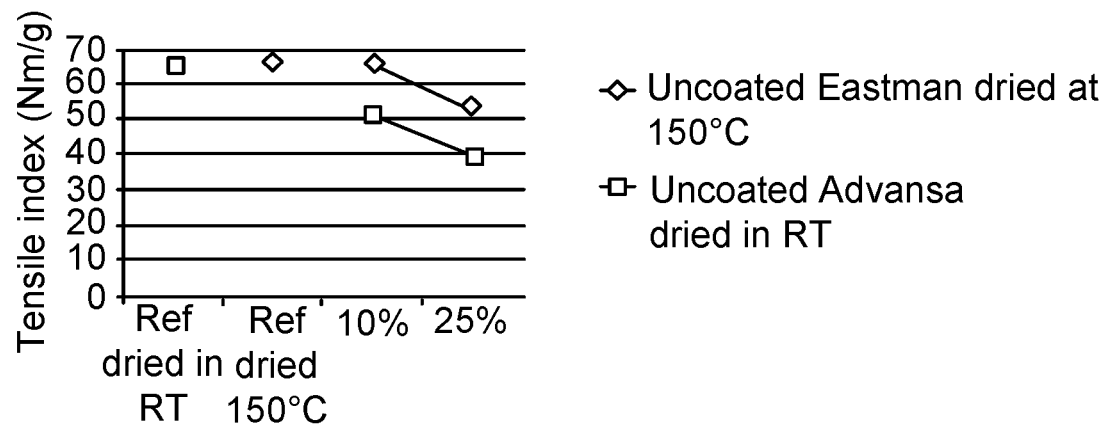
Figure 5C:
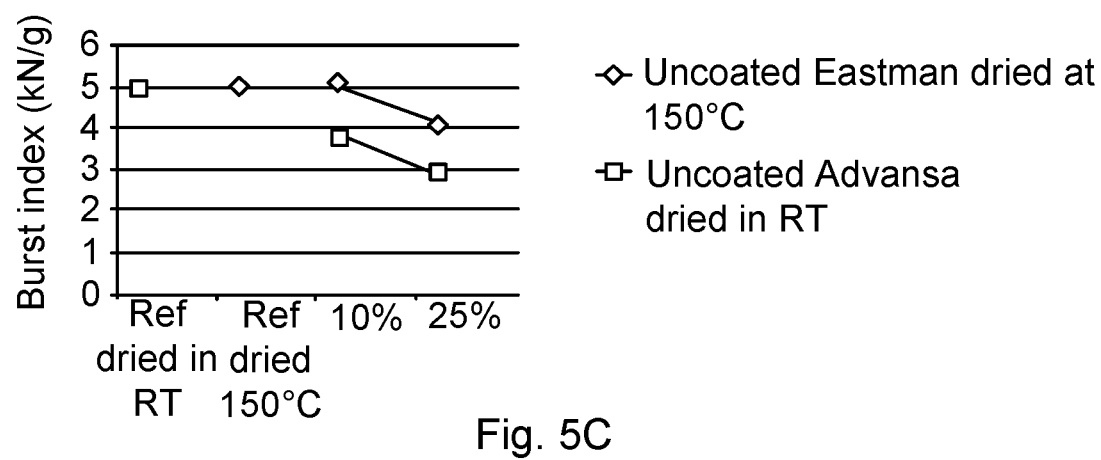
Figure 5D:
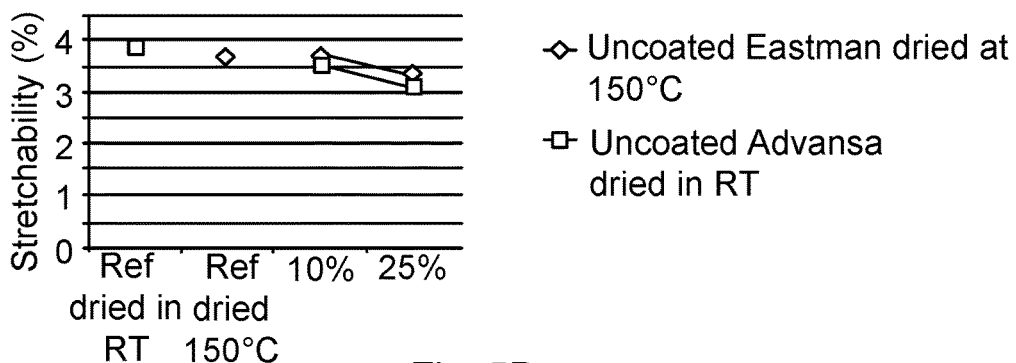

FIG. 5A shows that addition of the flat and short fibres has no significant impact on the tear index in case of uncoated sheets dried at 150° C. Further, such an addition has no or negative impact on the tensile index, burst index and stretchability (FIGS. 5B-D).

Figure 5E:
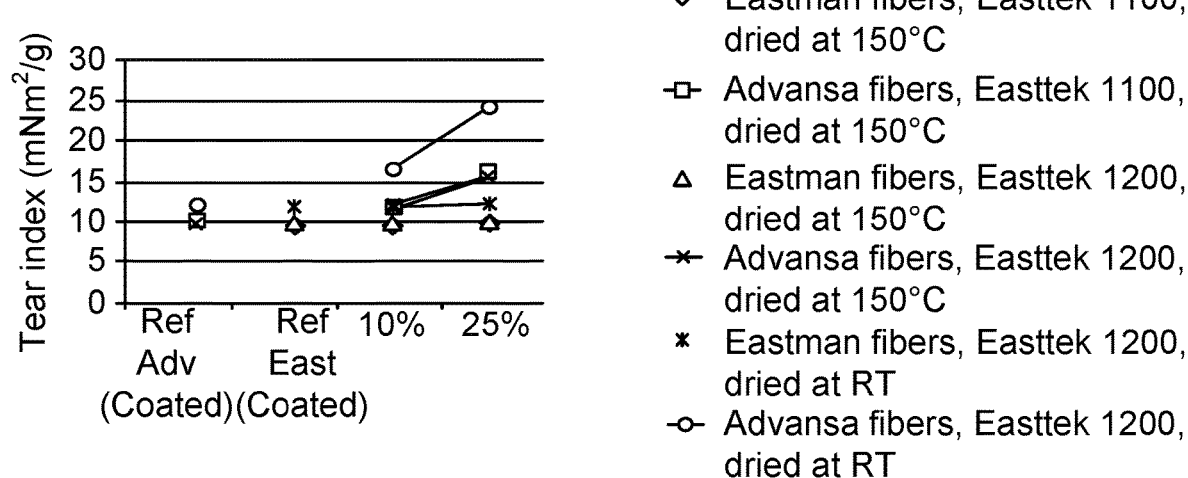
Figure 5F:
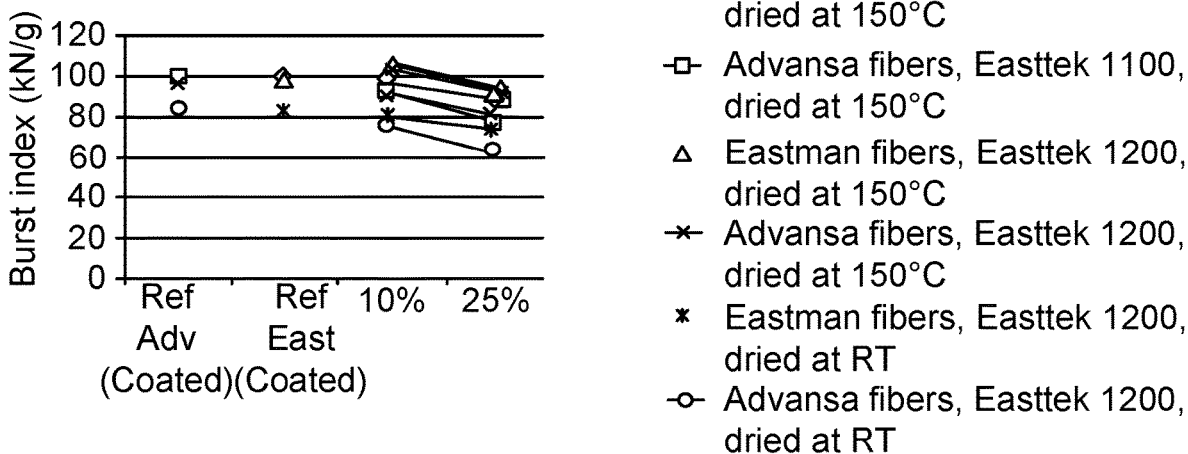
Figure 5G:
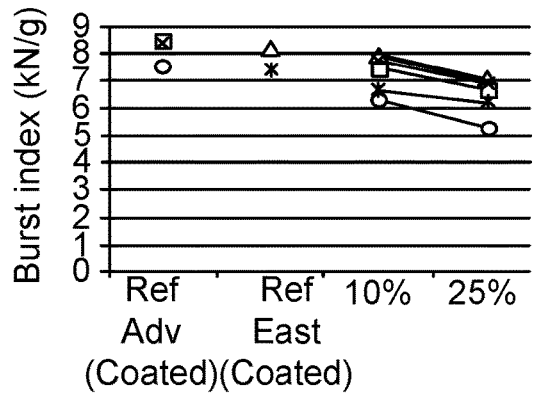
Figure 5H:
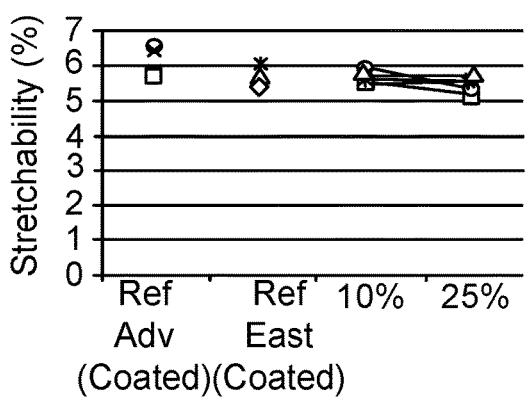

FIG. 5E shows that addition of the flat and short fibres has no significant impact on the tear index in case of coated sheets independent of the drying temperature. Further, such an addition has no or negative impact on the tensile index, burst index and stretchability (FIGS. 5F-H).

Summary of the Results from the Lab Trials Discussed Above

Figure 6:
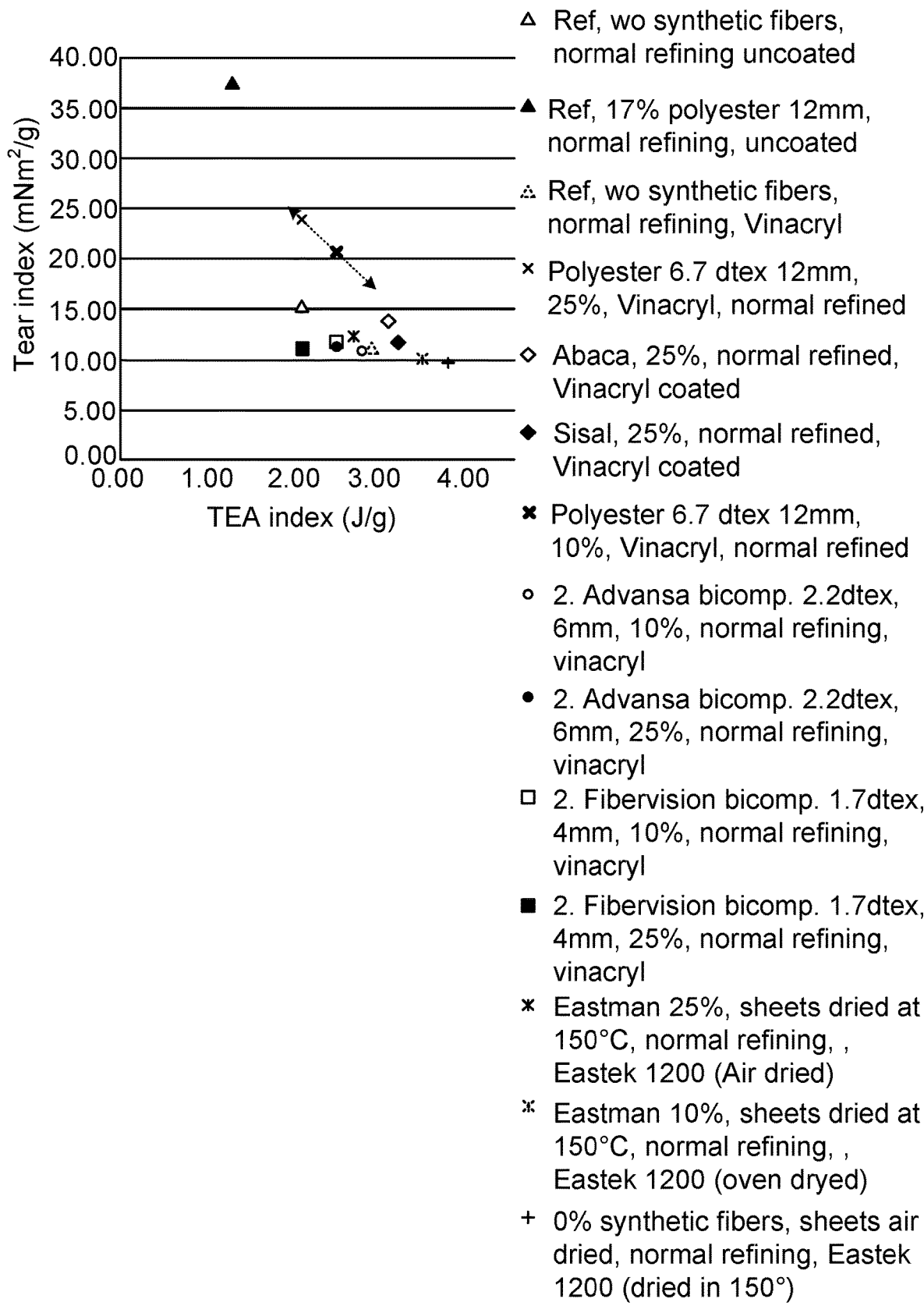
FIG. 6 shows a summary of results obtained in the "polyester (thickness) trial", the "natural fibres trial", "the bi-component fibre trial" and the "flat and short fibre trial". The double-headed arrow in FIG. 6 shows the direction in which the properties (tear index and TEA index) change when the amount of polyester fibre (6.7 dtex, 12 mm) is adjusted.

FIG. 6 shows that an increase of both tear index and TEA index was only obtained for the sheets reinforced with long and thick polyester fibres and coated with latex. The double-headed arrow in FIG. 6 shows the direction in which the properties change when the amount of fibres is adjusted. It is thus expected that a reduction of the amount of polyester fibres (6.7 dtex, 12 mm) from 10% to 5% would reduce the tear index (to a level that is still above that of the reference sheet), but further increase the TEA index.

Refining and Fibre Length Trial

Figure 7A:
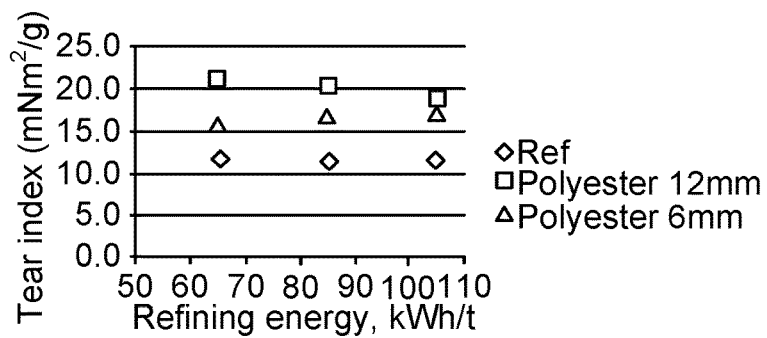
FIG. 7 shows results of the "Refining and fibre length trial" discussed in the Examples section. The y axes in FIG. 7 show the values of various paper properties of coated sheets to which 17% polyester fibre of different lengths have been added. The sheets also differ from each other in the amount of energy that has been used to refine the pulp in the sheets. Coated sheets without any polyester fibres are included as references.

FIG. 7A shows that the 12 mm polyester fibre increases the tear index to a greater degree than the 6 mm polyester fibre. This difference is particularly accentuated at the "normal" refining level of 65 kWh/t. The tear index of sheets comprising the 12 mm fibres was decreased when the reefing level was increased.

Figure 7B:
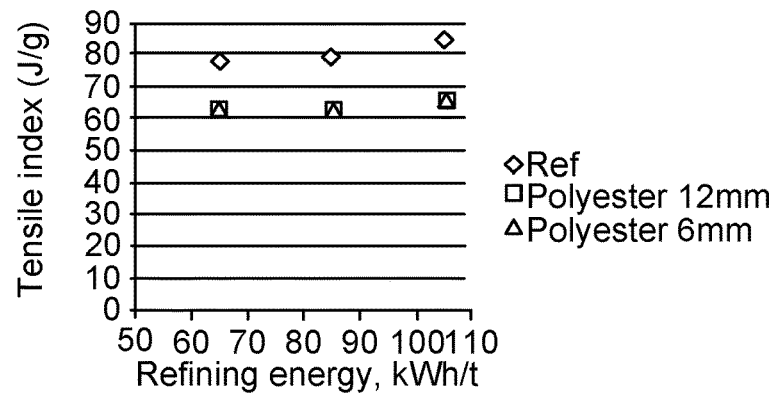
Figure 7C:
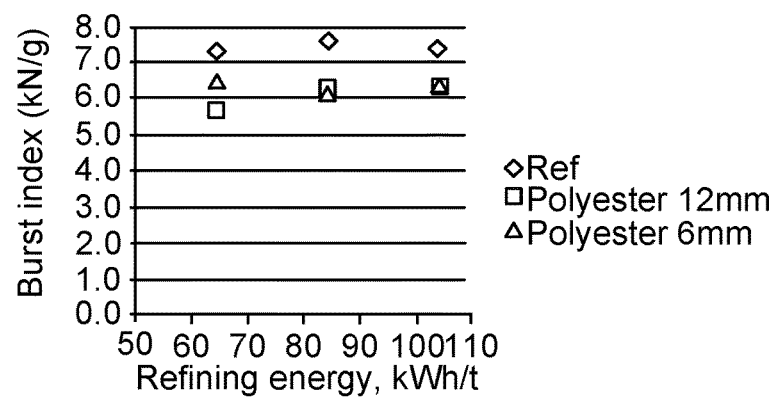

FIG. 7B shows that increased refining, as expected, results in higher tensile index for the reference sheet without polyester fibre. For the sheets comprising polyester fibre, there was however no or only an insignificant increase of the tensile index when the refining was increased. FIG. 7B also shows that the 12 mm polyester fibre does not decrease the tensile index to a greater degree than the 6 mm polyester fibre.

Figure 7D:
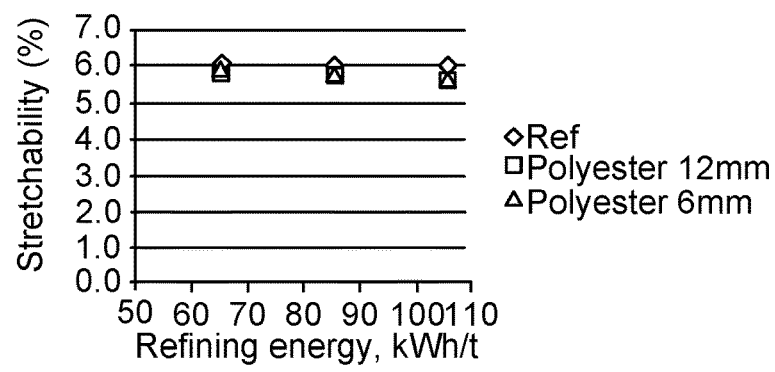

FIG. 7D shows that increased refining decreases stretchability to a greater degree for sheets comprising the polyester fibres.

It can be concluded from FIG. 7 that there is no need for high degrees of refining when polyester fibres are added and the paper is impregnated with a binder. Rather, the concept of the present disclosure may allow for a reduced degree of refining.

Starch, Wet Strength Agent and A-PAM Trial

This trial shows that the effects of increasing the amounts of starch and wet strength agent and adding A-PAM were small or insignificant.

Binder Type Trial

Figure 8:
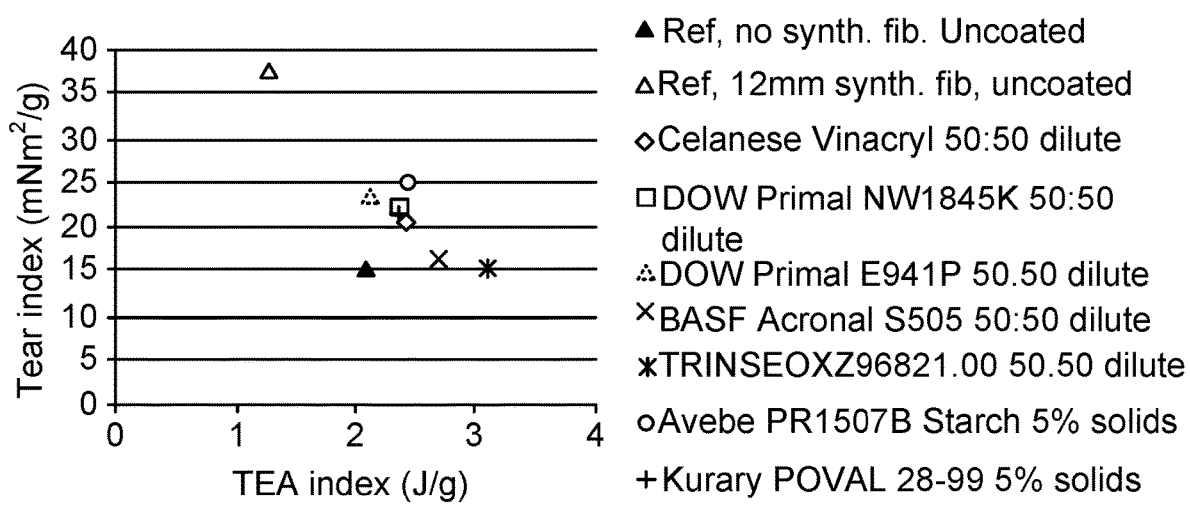
FIG. 8 shows results of the "binder type trial" discussed in the Examples section. Values for tear index and TEA index of sheets comprising 17% polyester fibre (12 mm) that have been coated with different binders are presented. Uncoated sheets with and without polyester fibres are included as references.

FIG. 8 shows that all binders more than compensated for the loss of TEA index caused by the addition of the 12 mm polyester fibres. However, the tear index was significantly reduced for all binders, in some cases almost back to the level of the uncoated reference sheet without any polyester fibres. If the polyester fibre had been thicker, the net gain in tear index would have been higher (see e.g. FIG. 1A).

The PVOH binder was however excluded from further trials due to its water solubility, which makes it unsuitable for the intended application.

Length and Thickness Trial

Figure 9:
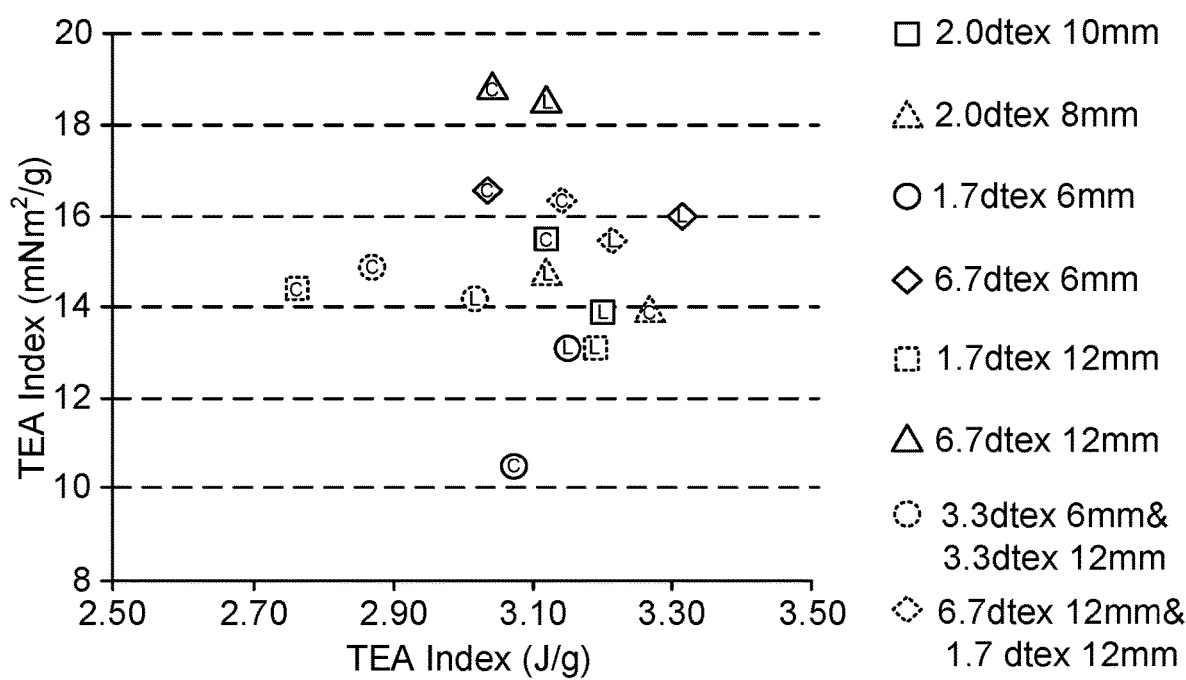
FIG. 9 shows results of the "length and thickness trial" discussed in the Examples section. Values for tear index and TEA index of sheets comprising 15% polyester fibre of different lengths and thicknesses are presented. Sheets without any polyester fibres are included as references. All sheets are coated with either latex ("L") or a combination of latex and starch ("C").

FIG. 9 shows i.a. that the highest tear index is obtained for the fibre having a thickness of 6.7 dtex and a length of 12 mm irrespective of the type of binder.

Air Resistance Trial

Figure 10:
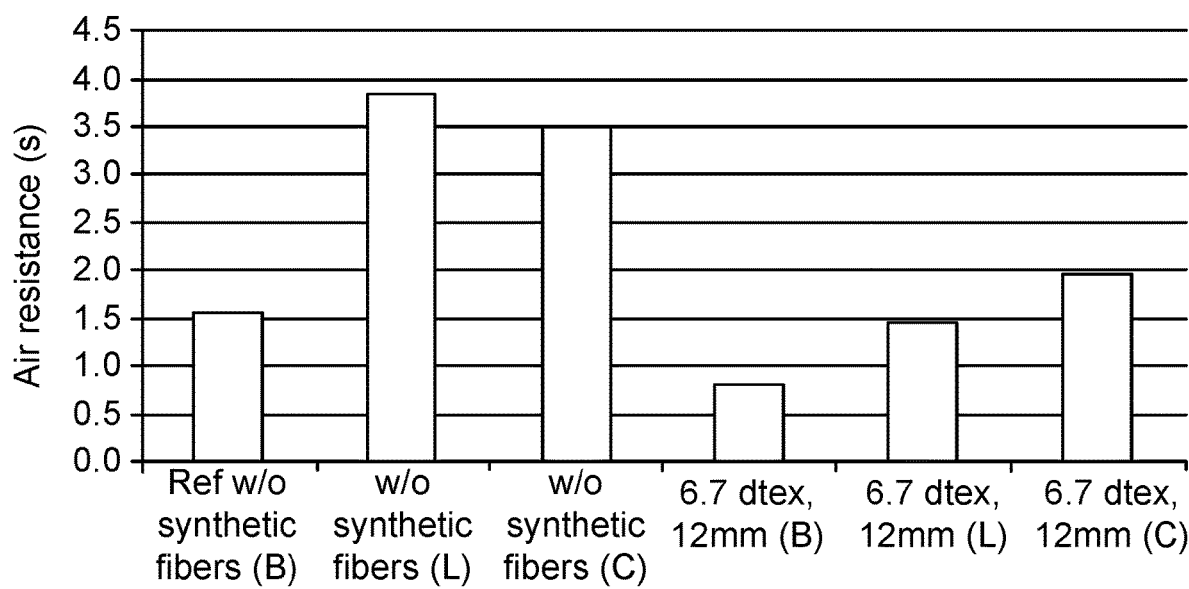
FIG. 10 shows results of the "Air resistance trial" discussed in the Examples section. Air resistance values for sheets comprising 15% of a polyester fibre (6.7 dtex, 12 mm) are presented. Sheets without any polyester fibres are included as references. The sheets are uncoated ("B"), coated with latex ("L") or coated with a combination of latex and starch ("C").

FIG. 10 shows that coating of a sheet without the polyester fibre drastically increases the air resistance (reduced the permeability). The figure further shows that addition of the polyester fibre (6.7 dtex, 12 mm) significantly reduces the air resistance in case of an uncoated sheet. It further shows that after the sheet comprising the polyester fibre was coated with the latex binder, the air resistance was still lower than for the uncoated reference sheet without polyester fibre. Also after coating the sheet comprising the polyester fibre with the starch/latex mixture, the air resistance was relatively low.

Results of Machine Trial

The properties of the paper product produced in the paper machine trial are presented in table 11, which also shows the properties of a commercial kraft paper for packaging of medical devices.

TABLE 11

The properties of the ("Inventive") paper produced in the paper machine trial are compared to those of a commercial reference paper produced on the same paper machine from a very similar pulp mixture (without synthetic fibres). "TS" means top side. "WS" means wire side.

| Paper Property | Unit | Inventive | Reference |
|---|---|---|---|
| Grammage | g/m² | 91.5 | 75.44 |
| Grammage (dry) | g/m² | ~88.7 | |
| Caliper | μm | 145 | 108 |
| Density | kg/m³ | 634 | 696 |
| Air resistance Gurley | s | | 22.3 |
| Porosity Bendtsen | ml/min | 612 | 549 |
| Tensile strength MD | kN/m | 7.97 | 8.75 |
| Tensile strength CD | kN/m | 4.57 | 4.36 |
| Tensile index MD | Nm/g | 87 | 116 |
| Tensile index CD | Nm/g | 50 | 58 |
| Tensile index CD/MD | % | 57 | 50 |
| Tensile stiffness MD | kN/m | 718 | 917 |
| Tensile stiffness CD | kN/m | 259 | 384 |
| Stretchability MD | % | 2.7 | 2.1 |
| Stretchability CD | % | 8.4 | 4.7 |
| TEA MD | J/m² | 146 | 121 |
| TEA CD | J/m² | 254 | 142 |
| TEA index MD | J/g | 1.6 | 1.6 |
| TEA index CD | J/g | 2.8 | 1.9 |
| TEA index geometric | J/g | 2.1 | 1.7 |
| Bursting strength | kPa | 414 | 389 |
| Burst index | kN/g | 4.5 | 5.2 |
| Tear strength MD | mN | 1845 | 850 |
| Tear strength CD | mN | 2241 | 969 |
| Tear index MD | mNm²/g | 20.2 | 11.3 |
| Tear index CD | mNm²/g | 24.5 | 12.8 |
| Tear index geometric | mNm²/g | 22.2 | 12.0 |
| Water absorption Cobb 60 TS | g/m² | 16 | |
| Water absorption Cobb 60 WS | g/m² | 17 | |
| Bending resistance MD (10 mm) | mN | 127 | 138 |
| Bending resistance CD (10 mm) | mN | 51 | 64 |
| Bending resistance geometric | mN | 80.0 | 94.3 |
| Bending resistance index geometric | Nm⁶/kg³ | 104.5 | 219.7 |

\*\*\*

The invention claimed is:

1. A paper for packaging of medical devices comprising 5-25 wt. % (dry) synthetic fibers comprising polyester and 3.0-10.0 wt. % (dry) of a synthetic latex binder or 1.0-5.0 wt. % (dry) of a starch binder, wherein the length of the synthetic fibers is 8-14 mm and the thickness of the synthetic fibers is 5.5-9.0 dtex and wherein the paper has a grammage according to ISO 536:2012 of 70-110 g/m²;
wherein the Bendtsen Porosity is measured according to ISO 5636-3:2013 is at least 400 ml/min.

2. The paper according to claim 1, which is a kraft paper.

3. The paper according to claim 1, which has a grammage according to ISO 536:2012 of 75-105 g/m².

4. The paper according to claim 1, wherein the Bendtsen Porosity is at least 400 ml/min.

5. The paper according to claim 1, wherein the amount of synthetic fibers is 8-15 wt. % (dry).

6. The paper according to claim 1, wherein the length of the synthetic fibers is 10-14 mm.

7. The paper according to claim 1, wherein the length of the synthetic fibers is 10-12 mm.

8. The paper according to claim 1, wherein a sheath portion of the synthetic fibers comprises polyester.

9. The paper according to claim 1, wherein the synthetic fibers are composed of polyester only.

10. The paper according to claim 1, wherein the amount of synthetic latex binder is 3.0-8.0 wt. % (dry).

11. The paper according to claim 1, wherein the geometric bending resistance index is 60-160 Nm⁶/kg³, which bending resistance is measured according to ISO 2493-1:2010 using a bending length of 10 mm and a bending angle of 15°.

12. The paper according to claim 1 wherein the Tensile Energy Absorption (TEA) index according to ISO 1924-3:2005 is at least 1.5 J/g in the machine direction (MD) and at least 2.4 J/g in the cross direction (CD).

13. The paper according to claim 1, wherein the tear index according to ISO 1974:2012 is at least 17.0 mNm²/g in the machine direction (MD) and at least 21.0 mNm²/g in the cross direction.

14. A method of producing a paper according to claim 1 in a paper machine, comprising the steps of adding the synthetic fibers comprising polyester to a pulp upstream a headbox of the paper machine, forming a paper web from the pulp and impregnating the paper web with the latex or starch binder.

15. The method of claim 14, wherein the impregnation is carried out using a size press, which forms part of the paper machine.

\* \* \* \* \*